(12) United States Patent
Ishii et al.

(10) Patent No.: US 6,447,790 B1
(45) Date of Patent: Sep. 10, 2002

(54) OILY MATERIAL COMPOSITION

(75) Inventors: Hiroji Ishii; Masako Koyama, both of Kawasaki; Tomomichi Ichikawa, Tokyo; Toshihiko Funakubo, Sayama, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/550,334

(22) Filed: Apr. 14, 2000

(30) Foreign Application Priority Data

Apr. 16, 1999 (JP) .......................................... 11-108950
Aug. 13, 1999 (JP) .......................................... 11-229048

(51) Int. Cl.⁷ ................................................ A61K 7/00
(52) U.S. Cl. ....................................... 424/401; 514/529
(58) Field of Search ........................... 424/401; 514/529

*Primary Examiner*—Michael A. Williamson
(74) *Attorney, Agent, or Firm*—Oblon, Spivak, McClelland, Maier & Neustadt, P.C.

(57) ABSTRACT

Herein is disclosed an oily material composition comprising, as effective components, both a specific alkyl or alkenyl ester of an N-long chain acyl neutral amino acid and a specific sterol ester of an N-long chain acyl neutral amino acid, or further an amphipathic substance in addition to the said two kinds of esters, which composition has both good moisturizing property and good moisture-permeating property, as well as good water-incorporating property and good emulsification stability, and shows a good feel on use (i.e., non-stickiness, good compatibility, no heavy touch and good spreadability), and shows, when incorporated in a cosmetic composition or a dermal external agent composition, an advantage of giving moisturizing property and moisture-permeating property as well as emulsification stability thereto and of giving a good feel on use.

8 Claims, No Drawings

OILY MATERIAL COMPOSITION

BACKGROUND OF THE INVENTION

1. [Technical Field of the Invention]

The present invention relates to an oily material composition which is characterized in containing (both of) the specific two kinds of esters of an N-long chain acyl neutral amino acid, or containing an amphipathic substance in addition to those esters, and also relates to a cosmetic composition or a dermal external agent composition which is characterized in containing both of the above-mentioned two kinds of esters of an N-long chain acyl neutral amino acid, or further containing an amphipathic substance in addition to those esters. More particularly, the present invention relates to an oily material composition which is characterized in containing two kinds of esters, i.e., an alkyl or alkenyl ester of an N-long chain acyl neutral amino acid where the alcoholic moiety is a branched-chain or a straight-chain saturated or unsaturated hydrocarbon group having 1–30 carbon atom(s), and a sterol ester of an N-long chain acyl neutral amino acid where the alcoholic moiety is a sterol residue, or further containing an amphipathic substance such as cholesterol in addition to those esters, and also relates to a cosmetic composition or a dermal external agent composition which is characterized in containing such two kinds of esters, or further containing an amphipathic substance such as cholesterol in addition to those esters.

2. [Prior Art]

Epidermal horny layer is an important organ which adjusts the evaporation of moisture from living body and protects the living body from various stimuli from outside. It has been known that the moisture in the epidermal horny layer is important so that the skin functions appropriately, and greatly contributes to moistening and softness of the skin. It has been known that, as the components for retaining the moisture in the horny layer, oil-soluble components in addition to the water-soluble ones such as NMF (natural moisturizing factor) play an important role. Thus, the oil-soluble components per se, besides an action of formation of oily film for suppressing the evaporation of moisture, retain the moisture to some extent (moisturizing property) whereby they have an action of retaining the moisture in the horny layer. It has been also known regarding the hair, that an appropriate amount of moisture is necessary for achieving a conditioning effect which is to maintain good health and gloss like in the case of the skin, and that oil-soluble components play an important role therefor.

Vaseline, lanolin and the like have been commonly used already as oily materials for cosmetics for the skin and the hair.

However, hydrocarbon oil itself such as vaseline has no action of retaining the moisture but it suppresses the evaporation of moisture mostly by formation of an oily membrane. Therefore, it has an excessive blocking property and there are disadvantages that it inhibits the normal physiological action of the skin and further that it gives stickiness, poor spreading (i.e., poor spreadability), poor compatibility, heavy touch, etc. during and after use. Lanolin which is commonly used as an oily agent having a moisturizing property, also has a blocking property since it suppresses the evaporation of moisture due to formation of an oily film like vaseline and, in addition, it has a disadvantage, like vaseline again, such as stickiness, poor spreading, poor compatibility, heavy touch, etc. during and after application. Accordingly, in order to eliminate such a disadvantage resulting from the blocking property, there has been a demand for the development of an oily material which forms an oily film having a moisture-evaporating property (moisture permeability) to some extent.

On the other hand, amino acid derivatives have been developed already as oily materials having a high safety. I.e., esters of N-long chain acyl neutral amino acids with higher alcohols having 12–30 carbon atoms and esters of N-long chain acyl acidic amino acids with higher alcohols having 8–22 carbon atoms are disclosed in Japanese Patent Publication (Kokoku) Nos. 12908/1979 and 12609/1981, respectively, as oily materials for skin and hair cosmetics and for external drugs.

However, because of the poor moisturizing property of the materials per se, there is a disadvantage that, when they are compounded with cosmetic compositions having a purpose of skin care and hair care, the moisturizing property of the resulting cosmetic compositions is poor. And their conditioning effect on the hair is insufficient as well.

In the meanwhile, an oily material having a sterol group has been developed as an oily material having a good moisturizing property. I.e., esters of fatty acids with sterols are disclosed in Japanese Patent Publication (Koukou) No. 23320/1984 and esters of N-long chain acyl neutral amino acids with sterols are disclosed in Japanese Patent Application Laid-Open (Kokai) No. 112514/1993.

However, although such esters having the sterol moiety improve the moisturizing property, there is a disadvantage that stickiness, poor spreading, poor compatibility, heavy touch, etc. during and after application result when they are compounded with cosmetics.

Further, there is a disclosure in Japanese Patent Application Laid-Open (Kokai) No. 275697/1995, of a mixture of an ester of an N-long chain acyl acidic amino acid with a sterol and an ester of an N-long chain acyl acidic amino acid with a higher alcohol having 8–22 carbon atoms as an oily material having a moisturizing property.

However, such an oily material is not always satisfactory due to the stickiness, poor spreading, poor compatibility, heavy touch, etc. during and after application of the resulting cosmetics when incorporated in a cosmetic composition.

To sum up, although lanolin, esters of fatty acids with cholesterol, esters of acyl acidic amino acids with cholesterol, etc. have been known already as oily agents (oily materials) having a moisturizing property, they have a disadvantage that they give unpleasant feel such as stickiness and heavy touch during use. Their moisturizing property is insufficient as well. There is an additional disadvantage in terms of the stability of cosmetic compositions and dermal external agent compositions in an emulsified state which are emulsions prepared by compounding with them.

SUMMARY OF THE INVENTION

[Problems to be Solved by the Invention]

Under the background of the prior art as mentioned hereinabove, it is an object of the present invention to provide an oily material composition having both high moisture-retaining property and high moisture permeability and also giving a good feel on use to a cosmetic composition or a dermal external agent composition when incorporated therein.

[Means for Solving the Problems]

The present inventors have carried out an intensive investigation for achieving such object and have found that an oily material composition composed of the two specific kinds of esters of N-long chain acyl neutral amino acids per se has both good moisture-retaining and good moisture-permeating properties as well as good feel on use (poor stickiness, good spreading, good compatibility and poor heavy touch), that it gives moisture-retaining and moisture-permeating properties as well as good feel upon use, to a cosmetic composition and a dermal external agent composition when it is incorporated therein and further that the above oily material composition, when compounded with an amphipathic substance such as cholesterol, can significantly improve the cosmetic composition and the dermal external agent composition in moisturizing property and water incorporating property. On the basis of such findings, the present inventors have accomplished the present invention.

Incidentally, water incorporating property stands for a property of incorporation of water by an oil-soluble substance as noted in lanolin and that can be an index of moisturizing property and emulsion stability. As mentioned already, vaseline and the like form an oily film (membrane) having a blocking property, have no affinity for the skin (poor compatibility) and show a poor organoleptic property. It has been also known that, when cholesterol is added to a hydrocarbon oil such as vaseline or liquid paraffin, the water incorporating property thereof is improved to some extent although that is not always sufficient (E. V. Truter: *J. Soc. Cosmet. Chem.*, 13, 173 (1962)). On the contrary, although the amphipathic substance used according to the present invention forms a film, it is well compatible to the skin. It is a new finding by the present inventors that water incorporating property and, as a result thereof, moisturizing property are significantly improved with such amphipathic substance. Incidentally, the emulsifying/stabilizing action with such amphipathic substance is believed to be due to the W/O-type emulsifying/stabilizing action.

Accordingly, the present invention relates to an oily material composition which comprises, as effective components, both an alkyl or alkenyl ester of an N-long chain acyl neutral amino acid represented by the following formula (1) and a sterol ester of an N-long chain acyl neutral amino acid represented by the following formula (2):

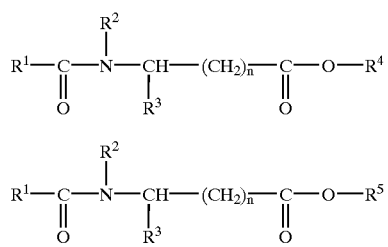

where, in the formulae (1) and (2), $R^1$s each independently represent a branched-chain or straight-chain alkyl or alkenyl group having 5–21 carbon atoms; in the formulae (1) and (2), $R^2$s each independently represent a hydrogen atom or an alkyl group having 1–3 carbon atom(s); in the formulae (1) and (2), $R^3$s each independently represent a hydrogen atom, a methyl group, an ethyl group, a branched-chain or straight-chain alkyl group having 3–4 carbon(s), a hydroxymethyl group or a hydroxyethyl group; $R^4$ represents a branched-chain or straight-chain alkyl or alkenyl group having 1–30 carbon atom(s); $R^5$ represents a sterol residue; and, in the formulae (1) and (2), n's each independently represent an integer of 0–2.

The present invention further relates to the oily material composition mentioned above which further comprises an amphipthic substance, in addition to the two kinds of esters mentioned above.

The present invention relates still further to a cosmetic composition or a dermal external agent composition which comprises the above-mentioned two kinds of esters, i.e., both an alkyl or alkenyl ester of an N-long chain acyl neutral amino acid represented by the above formula (1) and a sterol ester of an N-long chain acyl neutral amino acid represented by th above formula (2), as effective components.

As examples of the amphipathic substance can be mentioned sterols including cholesterol, phytosterol, etc., phospholipids, ceramides, fatty acids, etc. and, in view of the water incorporating property, sterols are preferred.

DETAILED DESCRIPTION OF THE INVENTION

Now the present invention will be further illustrated in greater detail.

The long chain acyl groups ($R^1COs$) appearing in the above-mentioned formulae (1) and (2) representing, in turn, the two kinds of N-long chain acyl neutral amino acid esters of the present invention, are each independently a straight-chain or branched-chain, saturated or unsaturated one having 6–22 carbon atoms. As the examples thereof, there can be mentioned those acyl groups which can be derived from capric acid, lauric acid, myristic acid, palmitic acid, stearic acid, behenic acid, linoleic acid, linolenic acid, oleic acid, isostearic acid, 2-ethylhexanoic acid, coconut oil fatty acid, palm kernel oil fatty acid, hydrogenated palm kernel oil fatty acid, beef tallow fatty acid and hydrogenated beef tallow fatty acid. Such fatty acids can be those which have a hydroxyl group. Preferred acyl groups can be caproyl group, lauroyl group, myristoyl group, palmitoyl group, stearoyl group and behenoyl group, and monovalent acid residues (acyl groups) which can be derived from coconut oil fatty acid, palm kernel oil fatty acid, hydrogenated palm kernel oil fatty acid and hydrogenated beef tallow fatty acid.

As the neutral amino acids constituting the neutral amino acid moieties of the N-long chain acyl neutral amino acid esters represented by the above-mentioned formulae (1) and (2), there can be mentioned each independently a neutral amino acid such as glycine, alanine, valine, leucine, isoleucine, serine, threonine, proline hydroxyproline, β-alanine, aminobutyric acid, aminocaproic acid, sarcosine or N-methyl-β-alanine. Among them, preferred ones are glycine, alanine, β-alanine, α-aminobutyric acid, γ-aminobutyric acid, sarcosine and N-methyl-β-alanine; more preferred ones are sarcosine, alanine, glycine and N-methyl-β-alanine; and most preferred ones are sarcosine and N-methyl-β-alanine. Those amino acids can be either in the optical active form or in the racemic form.

As the hydrocarbon group ($R^4$) constituting the alcohol moiety of the N-long chain acyl neutral amino acid ester represented by the above-mentioned formula (1), there can be mentioned a branched-chain or straight-chain, alkyl or alkenyl group having 1–30 carbon atom(s). Among them, as preferred ones, there can be mentioned those alkyl groups which can be derived, for example, from methanol, ethanol, propanol, isopropanol, butanol, tert-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, aralkyl alcohol, behenyl alcohol, hohoba alcohol, 2-hexadecyl alcohol, 2-octyldodecanol and isostearyl alcohol. Among them, preferred ones are lauryl alcohol, myristyl alcohol, cetyl alcohol, cetostearyl alcohol, stearyl alcohol, oleyl alcohol, aralkyl alcohol, behenyl alcohol, hohoba alcohol, 2-hexadecyl alcohol, 2-octyldodecanol and isostearyl alcohol; more preferred ones are lauryl alcohol, myristyl alcohol, cetostearyl alcohol, behenyl alcohol, hohoba alcohol, 2-hexadecyl alcohol, 2-octyldodecanol and isostearyl alcohol; and most preferred ones are behenyl alcohol, 2-hexadecyl alcohol, 2-octyldodecanol, isostearyl alcohol and behenyl alcohol.

As the sterol ($R^5OH$) constituting the alcohol moiety of the N-long chain acyl neutral amino acid ester represented by the above-mentioned formula (2), there can be mentioned cholesterol, dihydrocholesterol, sitosterol, campesterol, stigmasterol, phytosterol, lanosterol and hydrogenated products thereof. Among them, preferred ones are cholesterol, sitosterol, campesterol, stigmasterol, phytosterol and lanosterol; more preferred ones are cholesterol, sitosterol, campesterol, stigmasterol and phytosterol; and most preferred ones are cholesterol and phytosterol. They can be any of those derived from animals and plants and synthetic ones.

The N-long chain acyl neutral amino acid ester represented by the above formula (1) and the N-long chain acyl neutral amino acid ester represented by the above formula (2), which are effective components of the oily material composition of the present invention, are compounded preferably within a ratio-by-weight range of from 99:1 to 35:65, more preferably within a ratio-by-weight range of from 96:4 to 40:60 and, most preferably within a ratio-by-weight range of from 93:7 to 60:40. When the compounding ratio of the ester of N-long chain acyl neutral amino acid of the formula (1) is more than 99:1, a sufficient moisturizing property is not achieved, and whereas, when it is less than 35:65, stickiness results and that is not preferred.

The N-long chain acyl neutral amino acid esters which are effective components of the oily material composition of the present invention containing, as the affective components, the two kinds of N-long chain acyl neutral amino acid esters, can, for example, be prepared by condensation esterification of an N-long chain acyl neutral amino acid with an alkyl and/or alkenyl alcohol and a sterol by heat-dehydration either at atmospheric pressure or in vacuo. It is also possible to prepare them by means of azeotropic dehydration condensation reaction using a solvent such as toluene or by means of transesterification. The N-long chain acyl neutral amino acid which is to be used for the synthesis of such N-long chain acyl neutral amino acid ester need not be always a single compound, but can also be a mixture of N-long chain acyl neutral amino acids having different kinds of acyl groups or neutral amino acids. Likewise, the alcohol which is to be used for the synthesis of such N-long chain acyl neutral amino acid ester need not be always a single compound, but can also be a mixture of alcohols having different chain lengths.

Of course, it is also possible that an ester of an N-long chain acyl neutral amino acid with an alkyl and/or alkenyl alcohol and an ester of an N-long chain acyl neutral amino acid with a sterol are prepared separately, followed by mixing the two kinds of esters to prepare an oily material composition of the present invention.

The thus-prepared N-long chain acyl neutral amino acid esters may be used as the oily material composition of the present invention in the form of a reaction mixture per se unless that jeopardizes the effects of the invention or, if necessary or if desired, they may be purified by a known and common method used by the persons skilled in the art, such as recrystallization method or column chromatography method, to prepare an oily material composition of the present invention. Incidentally, it goes without saying that an N-long chain acyl neutral amino acid and salts thereof to be used as a starting material for the manufacture of the inventive esters, an alcohol which is allowed for cosmetic compositions, starting neutral amino acids, etc., accompanying the resulting N-long chain acyl neutral amino acid and salts thereof, a by-produced fatty acid, etc. are all usually contained in cosmetic compositions, and accordingly that they may be contained in the oily material composition within such amount that they do not deteriorate the effects of the present invention.

Incidentally, the N-long chain acyl neutral amino acid can be manufactured by a known method such as the so-called Schotten-Baumann reaction where a long chain fatty acid halide and an amino acid are allowed to react with each other in the presence of a basic catalyst (refer, for example, to Japanese Patent Publication (Kokoku) No.38681/1976).

When an amphipathic substance is, in addition to the two types of N-long chain acyl neutral amino acid esters represented by the above-mentioned formulae (1) and (2), compounded or incorporated, as another effective component, in the oily material composition and also in the cosmetic composition and the dermal external agent composition of the present invention, it is of course used in an amount whereby the effects by the use of the said amphipathic substance is achieved and, in the case of cholesterol for example, the said amount in terms of the ratio to the total amount of the above-mentioned two kinds of N-long chain acyl neutral amino acid esters can be 0.1–20%.

When an N-long chain acyl neutral amino acid sterol ester represented by the above formula (2) is synthesized from an N-long chain acyl neutral amino acid and a sterol, or when, as mentioned already, it is synthesized from an N-long chain acyl neutral amino acid alkyl and/or alkenyl alcohol and a sterol, and provided that unreacted sterol still remains in the synthetic reaction mixture (i.e., synthesized product), it is not necessary that an amphipathic substance is newly added insofar as such synthesized product containing the unreacted sterol, is used. However, it goes without saying that the said substance should be newly added in case the amount of the amphipathic substance remaining unreacted is little.

It has been mentioned already that, as a result of the use (compounding) of the amphipathic substance according to the present invention, there is a significant improvement in the moisturizing property and emulsification stability of the oily material composition and also of the cosmetic composition and the dermal external agent composition of the present invention.

The oily material composition of the present invention described hereinabove may be put on the market as it is, and can be subsequently used for the preparation of a cosmetic composition or a dermal external agent composition.

The oily material composition of the present invention can be, as an effective component, prepared into a cosmetic composition or a dermal external agent composition such as face-washing cream, face-washing foams, cleansing cream, massage cream, cold cream, moisture cream, milky lotion, cosmetic lotion, hand cream, pack, cosmetic agent for the skin of men, skin protecting agent for babies, foundation, lipstick, press powder, eye shadow, stick pomade, hair liquid, set lotion, permanent wave solution, hair cream, hair lotion, hair mousse, shampoo, hair rinse, hair conditioner, body shampoo, solid detergent, liquid detergent, antiperspirant, after-shaving cream, anti-sunburn cream, anti-sunburn oil, hair tonic, hair growing promoter, hairdye, bathing agent, pharmaceutical composition for external use, and shampoo and rinse for animals. There are no particular limitations to the preparation forms of such cosmetic compositions and dermal external agent compositions, and any of emulsified system, solution system, solubilized system, powder-dispersed system, two-layer system of water and oil, three-layer system of water, oil and powder, etc. may be used.

The oily material composition of the present invention is incorporated in the cosmetic composition of the present invention in an amount in terms of % by weight, of 0.05–30%, preferably, 0.1–10%, and more preferably, 0.5–5%, in the case of face-washing cream, face-washing foams, cleansing cream, hair liquid, set lotion, permanent wave solution, hair lotion, hair mousse, shampoo, hair rinse, hair conditioner, body shampoo, solid detergent, liquid detergent, antiperspirant, after-shaving cream, anti-sunburn cream, anti-sunburn oil, hair tonic, hair growth promoter, hairdye, bathing agent, shampoo for animals, rinse for animals, etc., and in an amount in terms of % by weight, of 0.05–60%, preferably, 0.1–30% and, more preferably, 0.5–20%, in the case of massage cream, cold cream, moisture cream, milky lotion, cosmetic lotion, hand cream, pack, cosmetics for the skin of men, skin protector for babies, foundation, lipstick, press powder, eye shadow, stick pomade, etc.

The oily material composition of the present invention is incorporated in the dermal external agent composition of the present invention in an amount in terms of % by weight, of 0.1–85%, preferably, 0.5–50% and, more preferably, 1–30%, in the case of jelly agent, ointment, etc., while, in the case of lotions, aerosols, etc., it is used in an amount in terms of % by weight, of 0.05–30%, preferably, 0.1–20% and, more preferably, 0.5–10%.

Instead of preparing previously an oily material composition as mentioned above from the two kinds of N-long chain acyl neutral amino acid esters as oily material or an amphipathic substance in addition thereto for the manufacture of the cosmetic composition or the dermal external agent composition, it is of course possible that the two kinds of N-long chain acyl neutral amino acid esters which have been manufactured separately, or an amphipathic substance in addition thereto, are directly compounded as the oily material with other components, if any, to prepare the cosmetic composition or the dermal external agent composition. In this case, the compounding ratio of the two kinds of N-long chain acyl neutral amino acid esters, and also the compounding ratio thereof to the amphipathic substance are the same as the already-mentioned compounding ratio of the two kinds of esters, and also as the compounding ratio thereof to the amphipathic substance, respectively. Further, the total compounding amount of the two esters, and also the total compounding amount thereof and the amphipathic substance are the same as those as has been described above in connection with the oily material composition of the present invention.

The cosmetic composition and the dermal external agent composition may be, according to the present invention, optionally compounded with any other oily materials which can be used for a cosmetic composition or a dermal external agent composition so far as the effects of the present invention are not deteriorated thereby. As such other oily materials, there can be mentioned those derived from animals and plants such as saturated or unsaturated fatty acids and higher alcohols obtained therefrom, squalane, castor oil and derivatives thereof, beeswax, lanolins including liquid and purified lanolin as well as derivatives thereof, macadamia nut oil, jojoba oil, carnauba wax, sesame oil, cacao oil, palm oil, mink oil, Japan wax, candelilla wax and whale wax; those derived from petroleum and minerals such as paraffin, microcrystalline wax, liquid paraffin, vaseline and ceresin; silicones such as methyl polysiloxane, polyoxyethylene methyl polysiloxane, polyoxypropylene methyl polyoxysiloxane, poly (oxyethylene, oxypropylene) methyl polysiloxane, methyl phenyl polysiloxane, polysiloxane modified with fatty acid, polysiloxane modified with aliphatic alcohol, polysiloxane modified with amino acid and the like; resin acid; fatty acid esters; ketones; etc.

When the oily material composition of the present invention composed of the two kinds of N-long chain acyl neutral amino acid esters or an amphipathic substance in addition thereto is used, or when such two kinds of esters or an amphipathic substance in addition thereto are concurrently used, in the manufacture of cosmetic compositions or dermal external agent composition, they have an effect of improving the stickiness, etc. of other oily materials and, therefore, the effects of the present invention can be fully achieved even in the case of a cosmetic composition or a dermal external agent composition where such a conventional oily material is compounded.

Further, various kinds of surface-active agents may be incorporated in the cosmetic composition and the dermal external agent composition in accordance with the present invention so far as the effects of the present invention are not deteriorated. As the surface-active agents, there can be mentioned anionic surface-active agents including N-long chain acyl amino acid salts such as N-long chain acyl acidic amino acid salts and N-long chain acyl neutral amino acid salts, N-long chain fatty acid acyl-N-methyltaurine salts, alkyl sulfates and alkylene oxide adducts thereof, fatty acid amide ether sulfates, metal salts and weak base salts of fatty acids, sulfosuccinsate type surface-active agents, alkyl phosphates and alkylene oxide adducts thereof, and alkyl ether carboxylic acids; nonionic surface-active agents including ether type surface-active agents such as glycerol ether and alkylene oxide adducts thereof, ester type surface-active agents such as glycerol esters and alkylene oxide adducts thereof, ether ester type surface-active agents such as sorbitan esters and alkylene oxide adducts thereof, ester type surface-active agents such as polyoxyalkylene fatty acid esters, glycerol esters, fatty acid polyglycerol esters, acylamino acid polyglycerol esters, sorbitan esters and sucrose fatty acid esters, alkyl glucosides, hardened castor oil pyroglutamic acid diester and ethylene oxide adducts thereof, and nitrogen-containing nonionic surface-active agents such as fatty acid alkanolamides and the like; cationic surface-active agents including aliphatic amine salts and quaternary ammonium salts thereof such as alkylammonium chlorides and dialkylammonium chlorides, aromatic quaternary ammonium salts such as benzalkonium salt, fatty acid acylarginine esters and alkyloxy hydroxypropylarginine salts; and amphoteric surface-active agents including betaine type surface-active agents such as carboxybetaine, aminocarboxylic acid type surface-active agents and imidazoline type surface-active agents.

In addition to the above-mentioned surface-active agents, various other additives which are ordinarily incorporated into a cosmetic composition or a dermal external agent composition, may be further added to, i.e., incorporated into, the cosmetic composition and the dermal external agent composition in accordance with the present invention so far as the effects of the present invention are not deteriorated. As such additives, there can be mentioned amino acids such as glycine, alanine, serine, threonine, arginine, glutamic acid, aspartic acid, leucine and valine; amino acid derivatives such as pyrrolidonecarboxylic acid and salts thereof, trimethylglycine and lauroyllysine; polyhydric alcohols such as glycerol, ethylene glycol, 1,3-butylene glycol, propylene glycol and isoprene glycol; water-soluble high molecular compounds such as polyamino acids including polyglutamic acid and polyaspartic acid and salts thereof, polyethylene glycol, gum arabic, alginates, xanthan gum, hyaluronic acid, hyaluronates, chitin, chitosan, water-soluble chitin, carboxyvinyl polymer, carboxymethyl cellulose, hydroxyethyl cellulose, hydroxypropyl trimethylammonium chloride, polydimethylmethylenepiperidium chloride, quaternary ammonium salts of polyvinylpyrrolidone derivatives, cationized protein, decomposed collagen and derivatives thereof, acylated protein and polyglycerol; sugar alcohols such as mannitol and alkylene oxide adducts thereof; lower alcohols such as ethanol and propanol; and others.

Furthermore, with regard to additives and pharmaceuticals which may be compounded with the cosmetic composition and the dermal external agent composition in accordance with the present invention, any of those which are commonly compounded with cosmetic compositions and dermal external agent compositions may be listed. As such dditives, there can be mentioned paraben derivatives and other antiseptics, perfume, dye, viscosity adjusting agent, pearlizing agent, antioxidant, bactericide, hinokitiol, hydrocortisone (V), ε-aminocarboxylic acid, azulene, allantoin, glycyrrhizic acid derivatives, β-glycyrrhetinic acid and other anti-inflammatory agents, sedatives, antifungal agents, agents for softening and removing the horny layer, coloring agents for skin, hormones, benzophenone derivatives, p-aminobenzoic acid derivatives, methoxycinnamic acid derivatives, salicylic acid derivatives, urocanic acid and derivatives thereof, 4-tert-butyl-4'-methoxybenzoylmethane, 2-(2'-hydroxy-5'-methylphenyl)-benzotriazole, methyl anthranilate, 2-ethylhexyl dimethoxybenzylidene-dioxoimidazolidinepropionate and other ultraviolet absorbers, pantothenic acid and derivatives thereof, placenta extract, allantoin and other hair growth promoters, arbutin, kojic acid, vitamin C and derivatives thereof and other whitening agents, antiperspirants, sweat deodorants, vitamins A, $B_1$, $B_2$, $B_6$, E and derivatives thereof and other vitamins, extract of an Ophelia, cepharanthine and other vasodilators, hydroquinone and derivatives thereof, γ-oryzanol, pH adjusting agents, traditional crude drugs of natural origin and other pharmaceuticals.

It goes without saying that the oily material composition of the present invention can be also incorporated into other products such as car wax.

There are no particular limitations for the manufacture per se of the cosmetic composition and the dermal external agent composition of the present invention, and known methods can be employed appropriately.

EXAMPLES

The present invention will now be further illustrated in detail by way of the following examples although the present invention is not limited thereto.

Manufacturing Example 1

Synthesis of N-myristoyl-N-methyl-β-alanine cholesteryl ester and N-myristoyl-N-methyl-β-alanine 2-hexadecyl ester N-Myristoyl-N-methyl-β-alanine (53 g; manufactured by Kawaken Fine Chemicals Co., Ltd.), 5 g of cholesterol and 42 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 62 g of an oily product as the filtrate.

The product (composition) was analyzed, whereupon the acid value was 0.03, the saponification value was 100, the pH (of a 1% suspension) was 6.09, the specific gravity ($D_{20}^{30}$) was 0.8959, and the nitrogen content (by the Kjeldahl method) was 2.335%.

Manufacturing Example 2

Synthesis of N-myristoyl-N-methyl-β-alanine cholesteryl ester and N-myristoyl-N-methyl-β-alanine 2-hexadecyl ester N-Myristoyl-N-methyl-β-alanine (52 g; manufactured by Kawaken Fine Chemicals Co., Ltd.), 10 g of cholesterol and 38 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 63 g of an oily product as the filtrate.

The product (composition) was analyzed, whereupon the acid value was 0.03, the saponification value was 98, the pH (of a 1% suspension), the specific gravity ($D_{20}^{30}$) was 0.9027, and the cholesterol content (by HPLC) was 2.17%.

IR (neat): 2925 $cm^{-1}$ (C—H), 1735 $cm^{-1}$ (ester), 1650 $cm^{-1}$ (amide).

Manufacturing Example 3

Synthesis of N-myristoyl-N-methyl-β-alanine cholesteryl ester and N-myristoyl-N-methyl-β-alanine 2-hexadecyl ester N-Myristoyl-N-methyl-β-alanine (51 g; manufactured by Kawaken Fine Chemicals Co., Ltd.), 20 g of cholesterol and 29 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 59 g of an oily product as the filtrate.

The product (composition) was analyzed, whereupon the acid value was 0.04, the saponification value was 96, the specific gravity ($D_{20}^{30}$) was 0.9178, and the cholesterol content (by HPLC) was 1.36%.

IR (neat): 2925 cm$^{-1}$ (C—H), 1735 cm$^{-1}$ (ester), 1650 cm$^{-1}$ (amide).

FAB-MS: 538,683 (M+H)+1.

Manufacturing Example 4

Synthesis of N-mixed fatty acid acyl alanine cholesteryl ester and N-mixed fatty acid acyl alanine 2-octyldodecyl ester N-Mixed fatty acid acyl alanine (40 g, the acyl groups composition (ratio by weight) being 11.3% of the capryl group, 9.4% of the caproyl group, 58.7% of the lauroyl group, 18.5% of the myristoyl group and 2.1% of the palmitoyl group), 20 g of cholesterol and 40 g of 2-octyldodecanol (manufactured by Kokyu Alcohol Kogyo K.K.) were charged in a 500-ml flask, and thereto was added 1 g of p-toluenesulfonic acid as the catalyst. The mixture was subjected to a dehydration condensation reaction in a nitrogen stream at 130° C. for 5 hours. After completion of the reaction, the reaction mixture was neutralized with 0.8 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off to give 59 g of an oily to pasty product as the filtrate.

The product (composition) was analyzed, whereupon the acid value was 0.27, the saponification value was 90, and the pH (of a 1% suspension) was 6.23.

Manufacturing Example 5

Synthesis of N-myristoyl-N-methyl-β-alanine cholesteryl ester and N-myristoyl-N-methyl-β-alanine 2-hexadecyl ester N-Myristoyl-N-methyl-β-alanine (48 g; manufactured by Kawaken Fine Chemicals Co., Ltd.), 30 g of cholesterol and 22 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 60 g of an oily product as the filtrate.

The product (composition) was analyzed, whereupon the acid value was 0.04, the saponification value was 86, and the cholesterol content (by HPLC) was 5.65%.

Manufacturing Example 6

Synthesis of N-myristoyl-N-methyl-β-alanine cholesteryl ester and N-myristoyl-N-methyl-β-alanine 2-octyldodecyl ester N-Myristoyl-N-methyl-p-alanine (47 g; manufactured by Kawaken Fine Chemicals Co., Ltd.), 20 g of cholesterol and 33 g of 2-octyldodecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 62 g of an oily product as the filtrate.

The product (composition) was analyzed, whereupon the acid value was 0.10, and the saponification value was 85.

Manufacturing Example 7

Synthesis of N-myristoyl-N-methyl-β-alanine phytosteryl ester and N-myristoyl-N-methyl-β-alanine 2-hexadecyl ester N-Myristoyl-N-methyl-β-alanine (50 g; manufactured by Kawaken Fine Chemicals Co., Ltd.), 20 g of phytosterol and 33 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 59 g of an oily product as the filtrate.

The product (composition) was analyzed, whereupon the acid value was 0.08, and the saponification value was 92.

Manufacturing Example 8

Synthesis of N-lauroyl-N-methyl-β-alanine cholesteryl ester and N-lauroyl-N-methyl-β-alanine 2-hexadecyl ester N-Lauroyl-N-methyl-p-alanine (48 g; manufactured by Kawaken Fine Chemicals Co., Ltd.), 20 g of cholesterol and 32 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 66 g of an oily product as the filtrate.

The product (composition) was analyzed, whereupon the acid value was 0.02, the saponification value was 94, and the cholesterol content (by HPLC) was 4.92%.

Manufacturing Example 9

Synthesis of a composition of N-lauroyl sarcosine cholesteryl ester and N-lauroyl sarcosine 2-hexadecyl ester N-Lauroyl sarcosine (47 g; manufactured by Kawaken Fine Chemicals Co., Ltd.), 20 g of cholesterol and 33 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 59 g of an oily product as the filtrate.

The product (composition) was analyzed, whereupon the acid value was 0.16, and the saponification value was 98.

Manufacturing Example 10

Synthesis of N-myristoyl alanine cholesteryl ester and N-myristoyl alanine 2-hexadecyl ester:

N-Myristoyl alanine (48 g), 20 g of cholesterol and 32 g of 2-hexadecanol (manufactured by Kokyu Alcohol Kogyo K.K.) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 63 g of an oily product as the filtrate.

The product (composition) was analyzed, whereupon the acid value was 0.04, and the saponification value was 94.

Manufacturing Example 11

Synthesis of a composition of N-myristoyl-N-methyl-β-alanine phytosteryl ester and N-myristoyl-N-methyl-β-alanine behenyl ester N-Myristoyl-N-methyl-β-alanine (46 g; manufactured by Kawaken Fine Chemicals Co., Ltd.), 15 g of phytosterol and 39 g of behenyl alcohol (manufactured by Kao Corporation) were charged in a 500-ml flask, and thereto was added 2 g of p-toluenesulfonic acid as the catalyst. The mixture was subjected to a dehydration condensation reaction in a nitrogen stream at 130° C. for 5 hours. After completion of the reaction, the reaction mixture was neutralized with 2 g of an aqueous solution (50%) of sodium hydroxide, washed with 300 g of deionized water and dehydrated under the condition of 60 mmHg and 95–105° C., to give 64 g of a solid product.

The product was analyzed, whereupon the acid value was 0.02, the saponification value was 86, and the phytosterol content (by HPLC) was 2.98%.

Referential Example 1

Synthesis of N-myristoyl-N-methyl-β-alanine 2-hexyldecyl ester

N-Myristoyl-N-methyl-β-alanine (55 g; manufactured by Kawaken Fine Chemicals Co., Ltd.) and 45 g of 2-hexyldecanol were charged in a 500-ml flask, and thereto was added 2 g of p-toluenesulfonic acid as the catalyst. The mixture was subjected to a reaction at 130° C. for 5 hours. After completion of the reaction, the reaction mixture was neutralized with 1.6 g of an aqueous solution (50%) of sodium hydroxide, the aqueous layer was removed therefrom, the residue was washed with 100 g of deionized water and dehydrated under the condition of 60 mmHg and 95–105° C., and the insoluble substances were filtered off with a filter paper to give 70 g of an oily product as the filtrate.

The product was analyzed, whereupon the acid value was 0.02, and the saponification value was 103.

IR (neat): 2940 cm$^{-1}$ (C—H), 1740 cm$^{-1}$ (ester), 1660 cm$^{-1}$ (amide).

Referential Example 2

Synthesis of N-lauroylalanine 2-octyldodecyl ester

N-Lauroylalanine (10 g) and 9.5 g of 2-octyldodecanol were charged in a 200-ml flask, and thereto was added 0.5 g of p-toluenesulfonic acid as the catalyst. The mixture was maintained at 130° C. for 3 hours for reaction. To the reaction mixture was added about 200 ml of a aqueous saturated solution of sodium hydrogen carbonate, and the resulting aqueous layer was removed. The oily layer was further washed with water. The extracted oily layer was well dried by adding 5 g of anhydrous magnesium sulfate thereto, and the magnesium sulfate was then filtered off to give 16 g (yield: 82%) of a liquid product.

IR (neat): 2940 cm$^{-1}$ (C—H), 1730 cm$^{-1}$ (ester), 1650 cm$^{-1}$ (amide).

Referential Example 3

Synthesis of N-myristoyl-N-methyl-β-alanine cholesteryl ester

N-Myristoyl-N-methyl-β-alanine (94 g; manufactured by Kawaken Fine Chemicals Co., Ltd.) and 104 g of cholesterol were charged in a 1000-ml flask, and thereto were added 303 g of toluene and 4 g of p-toluenesulfonic acid as the catalyst. The mixture was subjected to a dehydration condensation reaction at 130–140° C. for 6 hours. After completion of the reaction, the reaction mixture was neutralized with 206 g of an aqueous solution (2%) of sodium hydroxide, and the organic layer was washed with deionized water. A solid product obtained by evaporation of the toluene in vacuo was recrystallized from acetone and methanol successively to remove the unreacted substances or impurities such as cholesterol, and then filtered and dried to give 88 g of the desired product.

The product was analyzed, whereupon the cholesterol content (by HPLC) was 0.07%.

IR (KR): 2925 cm$^{-1}$ (C—H), 1715 cm$^{-1}$ (ester), 1650 cm$^{-1}$ (amide).

Referential Example 4

Synthesis of N-myristoylalanine cholesteryl ester

N-Myristoylalanine (34 g) and 43 g of cholesterol were charged in a 500-ml flask, and thereto were added 115 g of toluene and 1.5 g of p-toluenesulfonic acid as the catalyst. The mixture was subjected to a dehydration condensation reaction in a nitrogen stream at 130° C. for 5 hours. After completion of the reaction, the reaction mixture was neutralized with 100 g of an aqueous solution (2%) of sodium hydroxide. The organic layer was washed with deionized water, followed by evaporating the toluene in vacuo. The residue was dissolved in acetone and recrystallized from the acetone, whereby the unreacted substances or impurities such as cholesterol were removed, followed by filtering and drying to give 24 g of a powdery product.

The product was analyzed, whereupon the cholesterol content (by HPLC) was 0.03%.

IR (KB): 2925 cm$^{-1}$ (C—H), 1745 cm$^{-1}$ (ester), 1645 cm$^{-1}$ (amide).

Test Example 1 (Comparative Examples 1–4 and Examples 11–17)

Oily material compositions of the present invention were prepared using the N-long chain acyl neutral amino acid esters obtained in Referential Examples 1 and 3, and tested for moisturizing property (i.e., moisture-retaining property) and non-stickiness. Incidentally, each sample was, after diluted with vaseline to an extent of 50%, subjected to the test.

Moisturizing property and non-stickiness were tested according to an organoleptic evaluation by five professional panelists. Thus, each sample was applied in an appropriate amount onto the back of a hand of each panelist, and the organoleptic evaluation was conducted according to the evaluating criteria given below.

With regard to the moisturizing property, the average of the evaluations of the panelists according to the following evaluating criteria was calculated and, when the average was from 1.0 to 2.0, from 0.5 to less than 1.0, from 0 to less than 0.5 and from −1.0 to less than 0, the moisturizing property was judged to be good (oo), somewhat (o), a little (Δ) and none (x), respectively.

Criteria for Evaluation of Moisturizing Property
2: highly moisturizing;
1: moisturizing;
0: neither moisturizing nor non-moisturizing; and
−1: non-moisturizing.
Note: The evaluation was presumed to be 0 (blank) when vaseline was used as the oily material.

With regard to the non-stickiness, the average of the evaluations of the panelists according to the following evaluating criteria was calculated and, when the average was from 1.0 to 2.0, from 0.5 to less than 1.0, from 0 to less than 0.5 and from −1.0 to less than 0, the non-stickiness was judged to be non-sticky (oo), a little sticky (o), somewhat sticky (Δ) and sticky (x), respectively.

Criteria for Evaluation of Non-Stickiness
2: non-sticky;
1: a little sticky;
0: somewhat sticky; and
−1: sticky.
Note: The evaluation was presumed to be 0 (blank) when vaseline was used as the oily material.

The results are shown in the following Table 1. It is apparent from this table that, as compared with Comparative Examples, all of the (products of) Examples were better in terms of moisturizing property and non-stickiness.

TABLE 1

| | Compound of Ref. Ex. 1 (wt %) | Compound of Ref. Ex. 3 (wt %) | Moisturizing Property | Non-Stickiness |
|---|---|---|---|---|
| Comp. Ex. 1 | 100 | 0 | x | oo |
| Example 11 | 97 | 3 | Δ | oo |
| Example 12 | 95 | 5 | o | oo |
| Example 13 | 90 | 10 | oo | oo |
| Example 14 | 80 | 20 | oo | oo |
| Example 15 | 70 | 30 | oo | oo |
| Example 16 | 50 | 50 | oo | oo |
| Example 17 | 40 | 60 | oo | oo |
| Comp. Ex. 2 | 30 | 70 | oo | x |
| Comp. Ex. 3 | 10 | 90 | oo | x |
| Comp. Ex. 4 | 0 | 100 | o | x |

Test Example 2 (Comparative Examples 5–9 and Examples 18–20)

N-Long chain acyl neutral amino acid esters obtained in Manufacturing Examples and Referential Examples, lanolin and N-lauroylglutamic acid di(cholesteryl and 2-octyldodecyl) ester (an N-long chain acyl acidic amino acid ester described in Japanese Patent Application Laid-Open (Kokai) Hei-03/275697) were tested for moisturizing property, non-stickiness and moisture permeability. Each oily material was, after diluted with vaseline to an extent of 50%, subjected to the test.

Tests for moisturizing property and non-stickiness were carried out by the same methods as in Test Example 1.

Test for moisture permeability was carried out as follows. Thus, 25 mg of each sample was applied onto a cellophane sheet having a diameter of 7 cm, and the sheet was attached onto a moisture-permeable cup in which calcium chloride was placed (JIS Z-0208), and allowed to stand for 24 hours under the condition of 25° C. and 90% humidity. Thereafter, the permeability was calculated from the change in the weight of the calcium chloride. The figures are the values when the cellophane used was presumed to be blank (100%).

Evaluating Criteria for Moisture Permeability
oo: 25% or more;
o: from 20% to less than 25%;
Δ: from 15% to less than 20%; and
x: less than 15%.

The results are shown in the following Table 2. It is apparent from the table that, as compared with Comparative Examples, all of the (products of) Examples were better in terms of moisturizing property, non-stickiness and moisture permeability.

TABLE 2

| | Oily Material Composition or Oily Material | Moisturizing Property | Non-Stickiness | Moisture Permeability |
|---|---|---|---|---|
| Example 18 | Composition of Manuf. Ex. 3 | oo | oo | oo |
| Example 19 | Composition of Manuf. Ex. 5 | oo | oo | o |
| Example 20 | Composition of Manuf. Ex. 6 | oo | oo | o |
| Comp. Ex. 5 | Compound of Ref. Ex. 1 | x | oo | Δ |
| Comp. Ex. 6 | Compound of Ref. Ex. 2 | x | oo | Δ |
| Comp. Ex. 7 | Compound of Ref. Ex. 3 | o | x | o |
| Comp. Ex. 8 | Di-(cholesteryl and 2-octyldodecyl) N-lauroylglutamate | oo | x | o |
| Comp. Ex. 9 | Lanolin | o | x | Δ |

Test Example 3 (Comparative Examples 10–11 and Example 21)

Evaluation of the oily material applied onto hair was carried out by 5 professional panelists. A 0.5% by weight ethanolic solution of each oily material was prepared. Hair tufts were prepared from the hair of the same person where the tufts were made same in length and weight (2 g). Before the evaluating test, each tuft was washed with about 1000 ml (at 40° C.) of an aqueous 1% by weight solution of sodium polyoxyethylene lauryl ether sulfate, rinsed with warm water of 40° C. and well dried. Each tuft was dipped in the above-prepared ethanolic solution for 1 minute, well dried again and evaluated on the conditioning property (degree of good feel or touch) of the oily materials onto the hair. The average of the evaluations by the panelists according to the following evaluating criteria was calculated and, when the average was from 1.0 to 2.0, from 0.5 to less than 1.0 and from −1.0 to less than 0.5, the conditioning property was judged to be very good (oo), good (o) and poor (Δ), respectively.

Evaluating Criteria

2: very good;

1: good;

0: normal; and

−1: bad.

The results are shown in Table 3. It is apparent from the table that, as compared with Comparative Examples, the composition of Example showed a better conditioning property onto the hair.

TABLE 3

|  | Oily Material Composition or Oily Material | Conditioning Property onto Hair |
|---|---|---|
| Example 21 | Composition of Manufacturing Example 10 | oo |
| Comparative Example 10 | Compound of Referential Example 2 | Δ |
| Comparative Example 11 | Compound of Referential Example 4 | Δ |

Test Example 4 (Comparative Examples 12–14 and Examples 22–23)

Milky lotions containing the respective oily materials were prepared according to the formulations shown in the following Table 4. Milky lotions were, in an appropriate amount, applied onto the back of a hand of each panelist and an organoleptic evaluation was carried out according to the following evaluating criteria in terms of stickiness (non-sticky product being good), spreadability (spreadable product being good), compatibility, heavy touch (heavy touch being poor), and moisturized feel (moisturizing product being good). The average of the evaluations according to the following evaluating criteria by the panelists was calculated and, when the average was from 1.0 to 2.0, from 0.5 to less than 1.0, from 0 to less than 0.5 and from −1.0 to less than 0, the lotion property was judged to be very good (oo), good (o), ordinary (Δ), and poor (x), respectively.

Evaluating Criteria

2: very good;

1: good;

0: ordinary; and

−1: bad.

The results are also shown in Table 4. It is apparent from the table that, as compared with Comparative Examples, all of the (products of) Examples were better in each of the evaluating items.

TABLE 4

|  | Example 22 | Example 23 | Comparative Example 12 | Comparative Example 13 | Comparative Example 14 |
|---|---|---|---|---|---|
| Component A |  |  |  |  |  |
| Liquid Paraffin | 20 | 20 | 20 | 20 | 20 |
| Composition of Manuf. Ex. 1 | 3 |  |  |  |  |
| Composition of Manuf. Ex. 2 |  | 3 |  |  |  |
| Compound of Ref. Ex. 1 |  |  | 3 |  |  |
| Compound of Ref. Ex. 3 |  |  |  | 3 |  |
| Di(cholesteryl, behenyl, octyldodecyl) lauroylglutamate |  |  |  |  | 3 |
| Cetanol | 1 | 1 | 1 | 1 | 1 |
| Glyceryl stearate | 2 | 2 | 2 | 2 | 2 |
| POE(15) glyceryl monostearate | 4 | 4 | 4 | 4 | 4 |
| Butyl paraben | 0.1 | 0.1 | 0.1 | 0.1 | 0.1 |
| Component B |  |  |  |  |  |
| PEG 4000 | 3.1 | 3.1 | 3.1 | 3.1 | 3.1 |
| 1,3-Butylene glycol | 1.5 | 1.5 | 1.5 | 1.5 | 1.5 |
| Methyl paraben | 0.2 | 0.2 | 0.2 | 0.2 | 0.2 |
| pure water | balance | balance | balance | balance | balance |
| Organoleptic Evaluations |  |  |  |  |  |
| Stickiness | o | o | o | x | x |
| Spreadability | o | o | o | x | x |
| Compatibility | o | oo | Δ | x | Δ |
| Heavy touch | oo | oo | o | x | x |
| Moisturized feel | oo | oo | x | o | oo |

Test Example 5 (Examples 24–25 and Comparative Example 15)

Evaluation of the various oily materials onto hair was carried out by 4 professional panelists. A 0.5% by weight ethanolic solution of each oily material was prepared. Hair tufts were prepared from the hair of the same person where the tufts were made same in length and weight (2 g). Before the evaluating test, each tuft was washed with about 2000 ml (at 40° C.) of an aqueous 1% by weight solution of sodium polyoxyethylene lauryl ether sulfate, rinsed with warm water of 40° C. and well dried. Each tuft was dipped in the above-prepared ethanolic solution for 30 seconds, well dried again and evaluated on the moisturizing feel (if hair is moisturized, being good) and spreadability (spreadable one being good) of the oily materials onto the hair according to the following evaluating criteria. The average of the evaluations by the panelists according to the following evaluating criteria was calculated and, when the average was from 3.0 to 4.0, from 2.0 to less than 3.0, from 1.0 to less than 2.0 and from 0 to less than 1.0, they were evaluated as very good (oo), good (o), ordinary (Δ), and bad (x), respectively.

Evaluating Criteria

4: very good,

3: good,

2: ordinary,

1: poor, and

0: very bad.

The results are shown in the following Table 5. It is apparent from the table that, as compared with the Comparative Example, the products of Examples were better both in terms of moisturized feel and spreadability.

TABLE 5

| | Oily Material or Oily Material Composition | Moisturized Feel | Spreadability |
|---|---|---|---|
| Example 24 | Manufacturing Example 3 | ○○ | ○○ |
| Example 25 | Manufacturing Example 7 | ○○ | ○ |
| Comparative Example 15 | Lanolin | Δ | Δ |

Test Example 6 (Comparative Examples 16–19 and Examples 26–28)

Deionized water was added to 10 g of each of the compositions of Comp. Examples and Examples shown in the following Table 6, and the mixture was sufficiently stirred into a W/O emulsion. The maximum amount of water which could be added at that time whereby the emulsification for preparing a W/O emulsion was possible, was defined as water-incorporating ability. The water-incorporating ability was expressed as a percentage of the said maximum amount of water added to 10 g of the sample composition.

The results are also shown in the same table. It is noted from Table 6 that the compositions of Examples showed higher water-incorporating ability than those of the Comparative Examples.

TABLE 6

| | Comparative Examples | | | | Examples | | |
|---|---|---|---|---|---|---|---|
| Components | 16 | 17 | 18 | 19 | 26 | 27 | 28 |
| Compound of Ref. Ex. 1 | | | | 100 | 65 | 64.5 | |
| Compound of Ref. Ex. 2 | | | | | | | 65 |
| Compound of Ref. Ex. 3 | | | 20 | | 35 | 34 | 33 |
| Vaseline | 90 | 99 | 80 | | | | |
| Cholesterol | 3 | 1 | | | | 1.5 | 2 |
| Water Incorporating Ability (%) | 480 | 350 | 0 | 50 | 40 | 1000 | 1600 |

Example 29

A composition having a formulation of the following Table 7 was prepared by a conventional method. This cream had a good moisturizing property and showed a good feel in use (non-stickiness, compatibility, weight and spreadability).

TABLE 7

| (Oily Phase Components) | |
|---|---|
| Squalane | 4 |
| Cetyl octanoate | 8 |
| Composition of Manufacturing Example 11 | 2 |
| Dimethyl siloxane (10 cs) | 3 |
| Behenyl alcohol | 2 |
| Stearic acid | 2 |
| Propylene glycol monostearate | 1 |
| Glyceryl monostearate | 2 |
| Sorbitan monostearate | 1 |
| Butyl paraben | 0.1 |
| Vitamin E | q.s. |

TABLE 7-continued

| (Aqueous Phase Components) | |
|---|---|
| Sodium stearoylglutamate | 0.4 |
| Butylene glycol | 7 |
| Glycerol | 3 |
| Aqueous 1% solution of xanthan gum | 10 |
| Methyl paraben | 0.1 |
| Pure water | balance |

[Effects of the Invention]

The oily material compositions containing, as effective components, the two kinds of N-long chain acyl neutral amino acid esters of the present invention have both good moisturizing property and moisture-permeating property and show a good feel on use (i.e., non-stickiness, good compatibility, no heavy touch and good spreadability), and show, when incorporated in a cosmetic composition or a dermal external agent composition, an advantage of giving moisturizing property and moisture-permeating property thereto and of giving a good feel on use. When an amphipathic substance is used together with the above two kinds of N-long chain acyl neutral amino acid esters, water-incorporating property and, in turn, moisturizing property are further improved and stability of emulsion is improved as well.

What is claimed is:

1. An oily material composition which comprises, as effective components, both an alkyl or alkenyl ester of an N-long chain acyl neutral amino acid represented by the following formula (1) and a sterol ester of an N-long chain acyl neutral amino acid represented by the following formula (2):

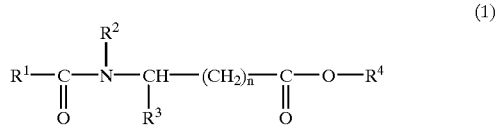

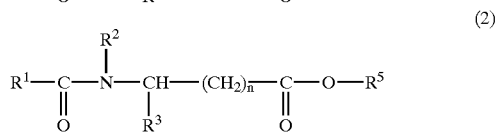

where, in the formulae (1) and (2), $R^1$s each independently represent a branched-chain or straight-chain alkyl or alkenyl group having 5–21 carbon atoms; in the formulae (1) and (2), $R^2$s each independently represent a hydrogen atom or an alkyl group having 1–3 carbon atom(s); in the formulae (1) and (2), $R^3$s each independently represent a hydrogen atom, a methyl group, an ethyl group, a branched-chain or straight-chain alkyl group having 3–4 carbon(s), a hydroxymethyl group or a hydroxyethyl group; $R^4$ represents a branched-chain or straight-chain alkyl or alkenyl group having 1–30 carbon atom(s); $R^5$ represents a sterol residue; and, in the formulae (1) and (2), n's each independently represent an integer of 0–2.

2. The oily material composition as set forth in claim 1, wherein the neutral amino acid moiety of the said alkyl or alkenyl ester of an N-long chain acyl neutral amino acid is a neutral amino acid selected from the group consisting of glycine, alanine, valine, leucine, isoleucine, serine, threonine, proline, hydroxyproline, β-alanine, aminobutyric acid, aminocaproic acid, sarcosine and N-methyl-β-alanine.

3. The oily material composition as set forth in claim 1 or 2, wherein the neutral amino acid of the said sterol ester of an N-long chain acyl neutral amino acid is a neutral amino acid selected from the group consisting of glycine, alanine, valine, leucine, isoleucine, serine, threonine, proline, hydroxyproline, β-alanine, aminobutyric acid, aminocaproic acid, sarcosine and N-methyl-β-alanine.

4. The oily material composition as set forth in claim 1, wherein the sterol of the said sterol ester of an N-long chain acyl neutral amino acid is a sterol selected from the group consisting of cholesterol, dihydrocholesterol, sitosterol, campesterol, stigmasterol, phytosterol and lanosterol.

5. The oily material composition as set forth in claim 1, which further comprises an amphipathic substance.

6. A cosmetic composition or a dermal external agent composition which comprises the composition as set forth in claim 1.

7. A cosmetic composition or a dermal external agent composition which comprises both an alkyl or alkenyl ester of an N-long chain acyl neutral amino acid represented by formula (1) and a sterol ester of an N-long chain acyl neutral amino acid represented by formula (2),

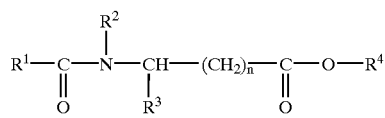
(1)

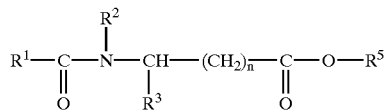
(2)

where, in the formulae (1) and (2), $R^1$s each independently represent a branched-chain or straight-chain alkyl or alkenyl group having 5–21 carbon atoms; in the formulae (1)and (2), $R^2$s each independently represent a hydrogen atom or an alkyl group having 1–3 carbon atom(s); in the formulae (1) and (2), $R^3$s each independently represent a hydrogen atom, a methyl group, an ethyl group, a branched-chain or straight-chain alkyl group having 3–4 carbon(s), a hydroxymethyl group or a hydroxyethyl group; $R^4$ represents a branched-chain or straight-chain alkyl or alkenyl group having 1–30 carbon atom(s); $R^5$ represents a sterol residue; and, in the formulae (1) and (2), n's each independently represent an integer of 0–2 effective components.

8. The cosmetic composition or the dermal external agent composition as set forth in claim 7, which further comprises an amphipathic substance.

* * * * *

UNITED STATES PATENT AND TRADEMARK OFFICE
CERTIFICATE OF CORRECTION

PATENT NO. : 6,447,790 B1  
DATED : September 10, 2002  
INVENTOR(S) : Hiroji Ishii et al.

It is certified that error appears in the above-identified patent and that said Letters Patent is hereby corrected as shown below:

Column 22,  
Line 22, "0-2 effective" should read -- 0-2, as effective --.

Signed and Sealed this

Twenty-first Day of January, 2003

JAMES E. ROGAN  
*Director of the United States Patent and Trademark Office*